(12) United States Patent
Castile

(10) Patent No.: US 8,451,455 B2
(45) Date of Patent: May 28, 2013

(54) METHOD AND APPARATUS INCORPORATING AN OPTICAL HOMODYNE INTO A SELF DIFFRACTION DENSITOMETER

(75) Inventor: Brett Castile, Del Mar, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 234 days.

(21) Appl. No.: 13/114,651

(22) Filed: May 24, 2011

(65) Prior Publication Data

US 2012/0300219 A1 Nov. 29, 2012

(51) Int. Cl.
*G01B 9/02* (2006.01)

(52) U.S. Cl.
USPC .......................................................... 356/521

(58) Field of Classification Search
USPC .................................. 356/441, 442, 517, 521
See application file for complete search history.

(56) References Cited

U.S. PATENT DOCUMENTS

| | | | |
|---|---|---|---|
| 4,068,956 A * | 1/1978 | Taboada | 356/434 |
| 4,544,271 A | 10/1985 | Yamamoto | |
| 5,255,069 A * | 10/1993 | Duarte | 356/521 |
| 5,903,393 A | 5/1999 | Kalibjian | |
| 6,118,535 A * | 9/2000 | Goldberg et al. | 356/521 |
| 6,128,080 A * | 10/2000 | Janik et al. | 356/491 |
| 6,469,787 B1 | 10/2002 | Meyer et al. | |
| 6,556,854 B1 | 4/2003 | Sato et al. | |
| 6,853,452 B1 | 2/2005 | Laufer | |
| 7,502,115 B2 | 3/2009 | Patel et al. | |
| 2008/0170225 A1 | 7/2008 | de Boer et al. | |
| 2008/0291444 A1 | 11/2008 | Donaldson et al. | |
| 2010/0277726 A1 | 11/2010 | Logan, Jr. et al. | |
| 2010/0309464 A1 | 12/2010 | Treado et al. | |
| 2010/0309465 A1 | 12/2010 | Liu et al. | |

FOREIGN PATENT DOCUMENTS

SU 1312466 A * 5/1987

* cited by examiner

*Primary Examiner* — Michael A Lyons
(74) *Attorney, Agent, or Firm* — Ronald E. Prass, Jr.; Prass LLP

(57) ABSTRACT

A method and apparatus incorporating an optical homodyne into a self-diffraction densitometer is disclosed. The method may include splitting a laser beam into four beams by passing the laser beam through a plurality of beam splitters, passing three beams of the four beams through a lens that focuses the three beams to minimum diffraction limited waist diameter and brings them to convergence at a convergence zone containing an analyte, generating a reference beam by passing a fourth beam of the four beams through an optical phase modulator, wherein if a medium within the convergence zone absorbs energy at a wavelength of the laser beam, a thermal representation of an interference pattern forms and spatial modulation of temperature results in a spatial modulation of refractive index, whereby a diffracted beam from energy of the three beams is produced into a propagation path of the reference beam, and passing the reference beam through the lens and the convergence zone such that the reference beam is coincident with the diffracted beam, wherein the reference beam and diffracted beams cyclically go in and out of relative phase and impinge on an optical detector.

26 Claims, 5 Drawing Sheets

METHOD AND APPARATUS INCORPORATING AN OPTICAL HOMODYNE INTO A SELF DIFFRACTION DENSITOMETER

BACKGROUND

1. Field of the Disclosed Embodiments

The disclosure relates to incorporating an optical homodyne into a self-diffraction densitometer.

2. Introduction

A self-diffraction densitometer may require the detection of a laser-like signal beam of very low power. When the self-diffraction process is implemented in the mid-infra-red part of the spectrum, it will be limited by the thermal noise out of the silicon infra-red detector. Even with optimized detectors that are thermo-electrically cooled, this thermal noise determines the upper limit of the signal to noise ratios that can be achieved by previous laser self-diffraction processes.

Thus, a need exists for a means by which the signal to noise ratio imposed by the available infra-red detectors can be overcome.

SUMMARY OF THE DISCLOSED EMBODIMENTS

A method and apparatus incorporating an optical homodyne into a self-diffraction densitometer is disclosed. The method may include splitting a laser beam into four parallel beams by passing the laser beam through a plurality of beam splitters, passing three beams of the four beams through a lens that focuses the three beams to minimum diffraction limited waist diameter and brings them to convergence at a convergence zone containing an analyte, generating a reference beam by passing a fourth beam of the four beams through an optical phase modulator, wherein if a medium within the convergence zone absorbs energy at a wavelength of the laser beam, a thermal representation of an interference pattern forms and spatial modulation of temperature results in a spatial modulation of refractive index, whereby a diffracted beam from energy of the three beams is produced into a propagation path of the reference beam. The reference beam is passed through the lens and the convergence zone such that the reference beam is coincident with the diffracted beam which has been cyclically phase modulated, wherein the reference beam and diffracted beams cyclically go in and out of relative phase and impinge on an optical detector.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION OF THE DISCLOSED EMBODIMENTS

Additional features and advantages of the disclosure will be set forth in the description which follows, and in part will be obvious from the description, or may be learned by practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth herein.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Aspects of the embodiments disclosed herein relate to method incorporating an optical homodyne into a self-diffraction densitometer, as well as corresponding apparatus and computer-readable medium.

Embodiments of the present disclosure provide a means by which to overcome the signal to noise ratio limitation imposed by the available infra-red detectors. This enables the detection of signal beams of far lower power. In turn, this enables the development of far more sensitive chemical or explosive vapor detectors than previously possible with existing state of the art self-diffraction processes.

The three input beam densitometer of embodiments of the present disclosure has advantages over a two input beam system. It can be used without confining an analyte region along a z axis. It produces significantly higher SNR if analyte region is unconfined and is readily suited for the application of an optical homodyne. Further, inclusion of the optical homodyne as provided herein has the following advantages: potential for a very significant improvement in SNR and eliminates the need for a mechanical beam chopper and lock-in amplifier.

Although not limited in this respect, embodiments of the present disclosure should work at all optical wavelength.

Figure 1:
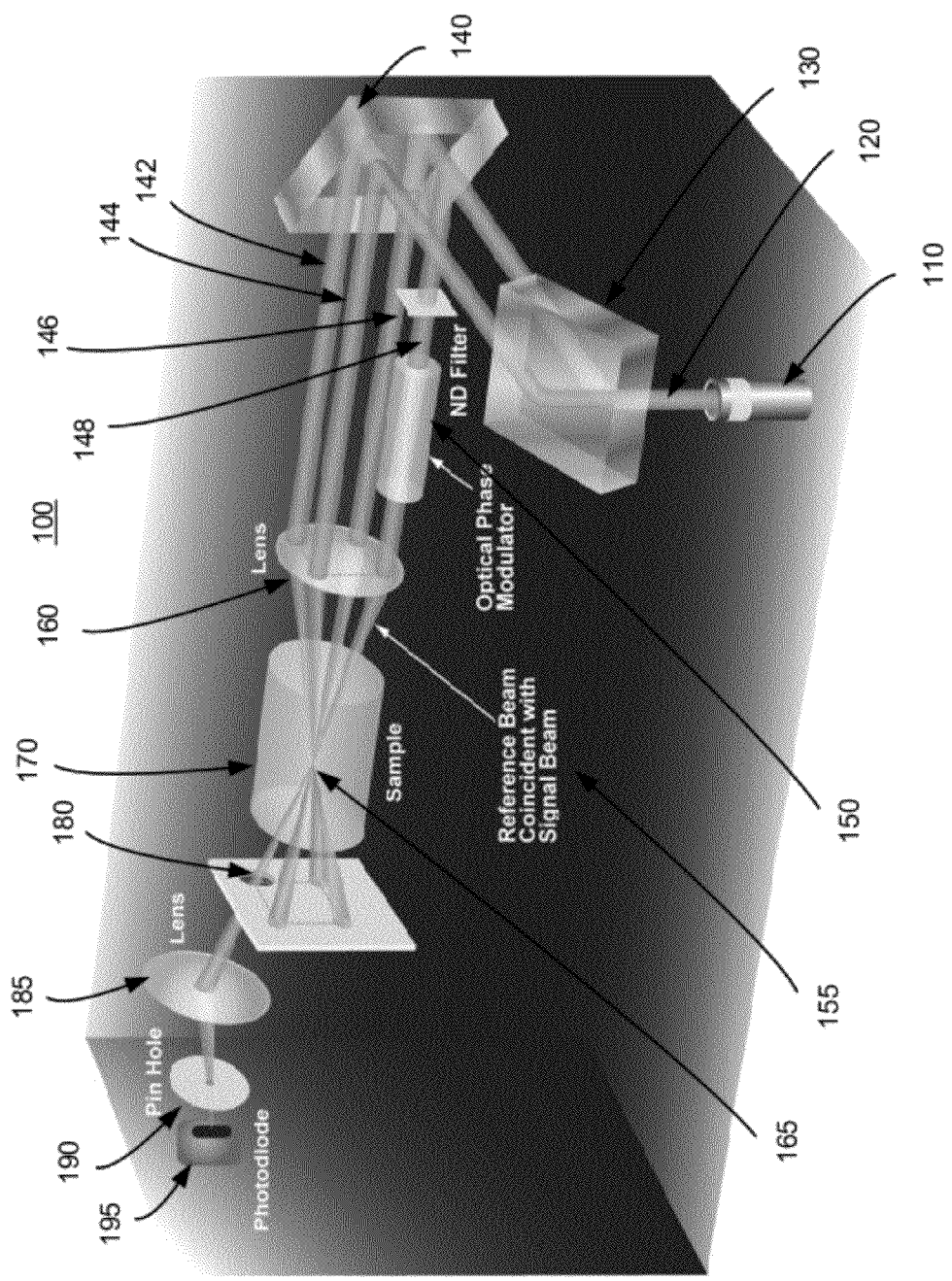
FIG. 1 is a diagram of an exemplary self-diffraction densitometer incorporating an optical homodyne in accordance with a possible embodiment of the disclosure.

FIG. 1 is a diagram of an exemplary self-diffraction densitometer incorporating an optical homodyne 100 in accordance with a possible embodiment of the disclosure. Previously, optical homodyne detection has not been used in conjunction with the self-diffraction process described herein. Self-diffraction densitometer incorporating an optical homodyne 100 may include a plurality of beam splitters 130, 140 for splitting laser beam 120 generated by laser 110 into four beams 142, 144, 146 and 148. These beams may be four inherently parallel beams.

A lens 160 may pass three beams 142, 144 and 146 of the four beams 142, 144, 146 and 148 to focus the three beams 142, 144 and 146 to minimum diffraction limited waist size and bring them to convergence at a convergence zone 165 containing an analyte 170. The beam convergence zone may contain a three dimensional interference pattern. An optical phase modulator 150 may pass a fourth beam 148 of the four beams 142, 144, 146 and 148 to generate a reference beam 155.

If a medium within the convergence zone 165 absorbs energy at a wavelength of the laser beam 120, a thermal representation of an interference pattern forms and spatial modulation of temperature results in a spatial modulation of refractive index. In an embodiment of the present disclosure, a diffracted beam 180 from energy of the three beams 142, 144, 146 is produced into a propagation path of the reference beam 155.

The reference beam 155 passes through the lens 160 and the convergence zone 165 such that the reference beam 155 is coincident with the diffracted beam 180 and the reference beam 155 and diffracted beams 180 cyclically go in and out of relative phase. The reference beam 155 and the diffracted beam 180 impinge on an optical detector, which, in an embodiment of the disclosure, may be a photodiode 195.

A second lens 185 may be incorporated to concentrate and direct the reference 155 and diffracted 180 beams through a pin hole 190 or other optics designed to collect these beams prior to impinging the optical detector 195. In an embodiment of the present disclosure, the optical phase modulator 150 may be a resonant gas phase acousto-optic modulator.

Figure 2:
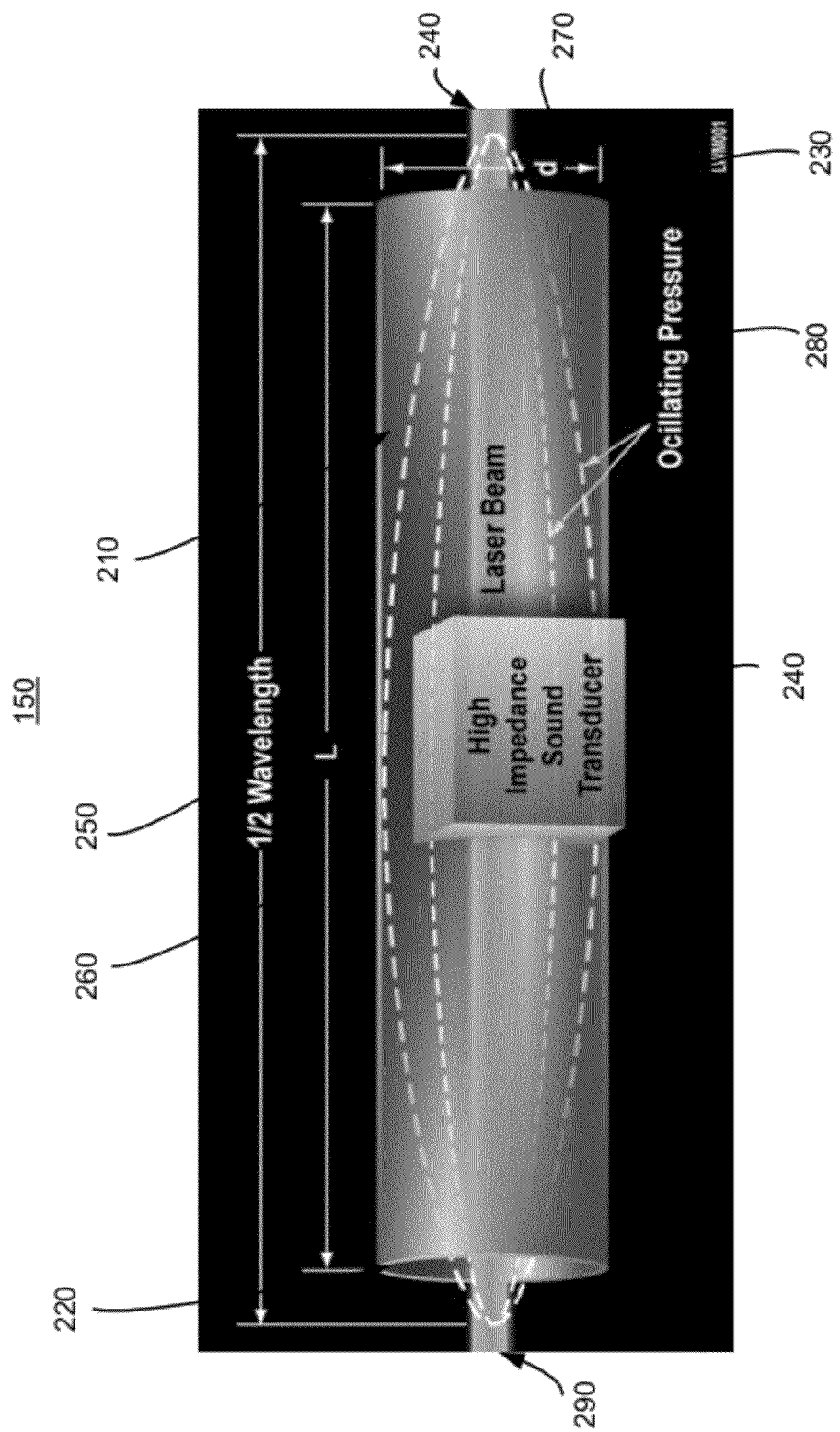
FIG. 2 is a is a diagram of an exemplary resonant gas phase acousto-optic modulator in accordance with a possible embodiment of the disclosure.

FIG. 2 is a is a diagram of an exemplary resonant gas phase acousto-optic modulator 150 which may be used in the self-diffraction densitometer incorporating an optical homodyne in accordance with a possible embodiment of the disclosure. The resonant gas phase acousto-optic modulator may include a tube 210 open to air at both ends 220, 230 through which a laser beam 240 is passed longitudinally. An acoustic transducer 240 within the tube may set air inside the tube 210 into resonant acoustic oscillation. The refractive index of air varies somewhat with air pressure. Thus, a laser beam 240 passed through the tube will have imposed on it a periodic sinusoidal phase modulation with the period of the acoustic resonance. The phase modulated beam is shown at 290 at the output of tube 210.

In an embodiment of the disclosure, the acoustic transducer may be near a center of the tube 210 and the acoustic transducer 240 may be used to excite the resonant acoustic oscillation within the tube 210 to create acoustic oscillations such that one acoustic wavelength 250 is slightly longer than twice the tube 210 length 260.

The acoustic pressure oscillates at high amplitude near the center of the tube 210 and tapers to near zero at both ends 220, 230 of the tube 210. The refractive index of the air inside the tube 210 varies periodically with air pressure, thereby imposing a sinusoidal phase modulation with a period of acoustic resonance on the laser beam passed lengthwise through the tube 210.

Optical phase modulators of various types are commercially available. However, they are not optimum for the self-diffraction densitometer incorporating an optical homodyne 100 provided herein. They generally use an electro-optic crystal. This presents optical surfaces through which the beam must pass. Because the present disclosure may ultimately need to detect optical beams of miniscule amplitude, it is important to minimize the number of optical surfaces through which beam 148 passes which inevitably scatters some of the monochromatic laser light. The resonant gas phase acousto-optic modulator 150 presents no optical surfaces through which the beam 148 passes and therefore keeps spurious scattering to a minimum. Further, existing solid state optical phase modulators inevitably produce some, although small, residual amplitude modulation.

In an embodiment of the present disclosure, reference beam 155 of the self-diffraction densitometer incorporating an optical homodyne 100 is attenuated so that it does not drive the optical detector 150 out of its proper operating range. The diffracted beam 180 may be a signal beam which indicates the extent to which the medium absorbs energy at the wavelength of the laser 110. Further, in an embodiment of the disclosure the reference beam 155 coincident with the signal beam 180 may have the same wave front curvature and essentially a same divergence.

Optical detector 195 may be a "square law" detector and may produce an output current that is proportional to the rate at which photons are intercepted, that is to the square of the amplitude of the electrical component of the optical field. Photocurrent thus depends on relative phase between the reference beam 155 and the coincident signal beam 180, if there is one. The nonlinear mixing of the reference beam 155 coincident with the diffracted beam 180 may produce low frequency components in an output current that enable homodyne detection. In an embodiment of the present disclosure, the D.C. components from the output current are removed and the output current contains A.C. components proportional in amplitude to a product of the reference beam 155 and signal beam 180 amplitudes. High reference beam amplitude yields high amplitude of A.C. photocurrent components but does not affect thermal noise out of the optical detector 195. The reference beam 155 power may be raised to a point where shot noise on the reference beam 155 overpowers the optical detector's 195 thermal noise with a corresponding increase in signal beam 180 power to enable improvement in signal to noise ratio.

Figure 3:
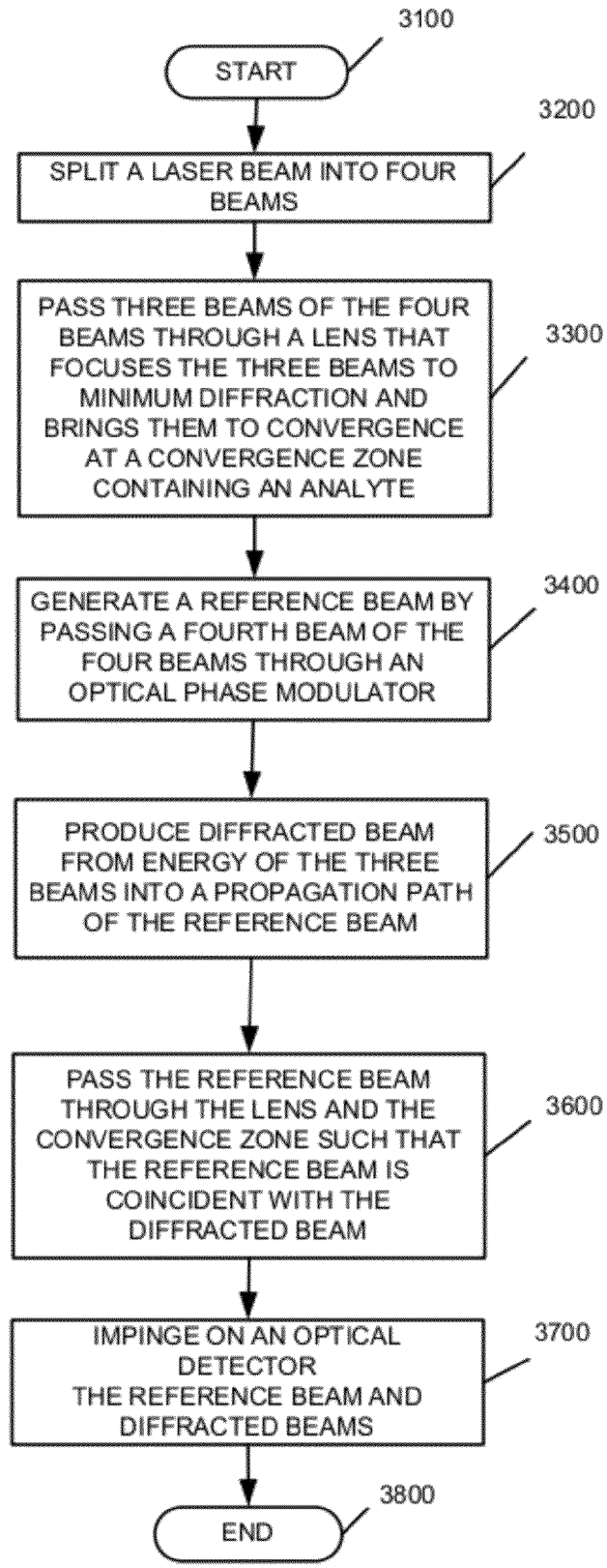
FIG. 3 is an exemplary flowchart illustrating a method incorporating an optical homodyne into a self-diffraction densitometer in accordance with one possible embodiment of the disclosure.

FIG. 3 is an exemplary flowchart illustrating a method incorporating an optical homodyne into a self-diffraction densitometer 100 in accordance with one possible embodiment of the disclosure. The process may begin at step 3100 and may continue to step 3200, where laser beam 120 is split into four beams 142, 144, 146 and 148 by passing the laser beam through a plurality of beam splitters 130, 140.

At step 3300, three beams 142, 144, 146 of the four beams 142, 144, 146 and 148 pass through a lens that focuses the three beams 142, 144, 146 to minimum diffraction limited waist size and brings them to convergence at a convergence zone 165 containing an analyte 170.

At step 3400, a reference beam is generated by passing a fourth beam 148 of the four beams 142, 144, 146 and 148 through an optical phase modulator 150. As set forth above, if a medium within the convergence zone absorbs energy at a wavelength of the laser beam, a thermal representation of an interference pattern forms and spatial modulation of temperature results in a spatial modulation of refractive index.

At step 3500, a diffracted beam 180 from energy of the three beams 142, 144, 146 is produced into a propagation path of the reference beam 155.

At step 3500, the reference beam is passed the through the lens 160 and the convergence zone 165 such that the reference beam 155 is coincident with the diffracted beam 180.

At step 3600, the reference beam 155 and diffracted beam 180 go cyclically in and out of relative phase and impinge on an optical detector 195.

Figure 4:
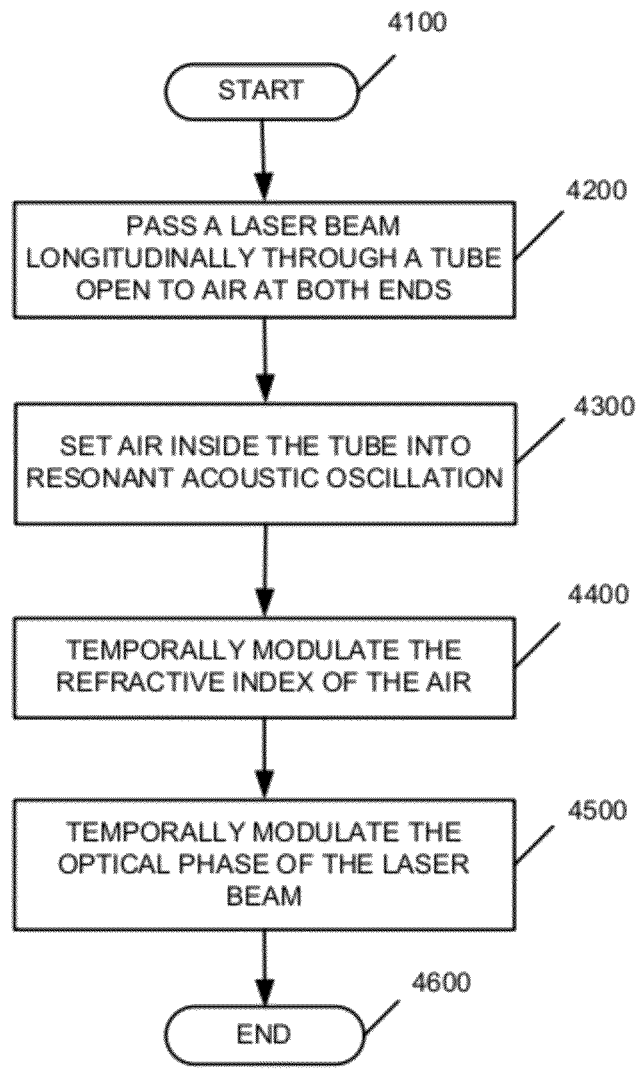
FIG. 4 is an exemplary flowchart illustrating the method of operation of a resonant gas phase acousto-optic in accordance with one possible embodiment of the disclosure.

As an optical phase modulator 150 may be a resonant gas phase acousto-optic modulator, FIG. 4 is an exemplary flowchart illustrating the method of operation of the resonant gas phase acousto-optic in accordance with one possible embodiment of the disclosure. The process may begin at step 4100 and may continue to step 4200, where a laser beam is passed longitudinally through a tube 210 open to air at both ends 220, 230.

At step 4300 air inside the tube 210 is set into resonant acoustic oscillation. At step 4400, the refractive index of the air is temporally modulated. At step 4500, the optical phase of the laser beam is thus temporally modulated.

The self-diffraction densitometer incorporating an optical homodyne 100 illustrated in FIG. 1 and resonant gas phase acousto-optic modulator in FIG. 2 and associated methods described in FIGS. 3 and 4 and the related discussion were intended to provide a brief, general description of a suitable environment in which the invention may be implemented. Although not required, the invention is described below, at least in part, in the general context of computer-executable instructions, such as program modules, being executed by the self-diffraction densitometer incorporating an optical homodyne 100, controlled by a general purpose computer, for example.

Generally, program modules include routine programs, objects, components, data structures, etc. that perform particular tasks or implement particular abstract data types. Moreover, those skilled in the art will appreciate that other embodiments of the invention may be practiced in communication network environments with many types of communication equipment and computer system configurations, including personal computers, hand-held devices, multi-processor systems, microprocessor-based or programmable consumer electronics, and the like.

Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Embodiments within the scope of the present disclosure may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Figure 5:
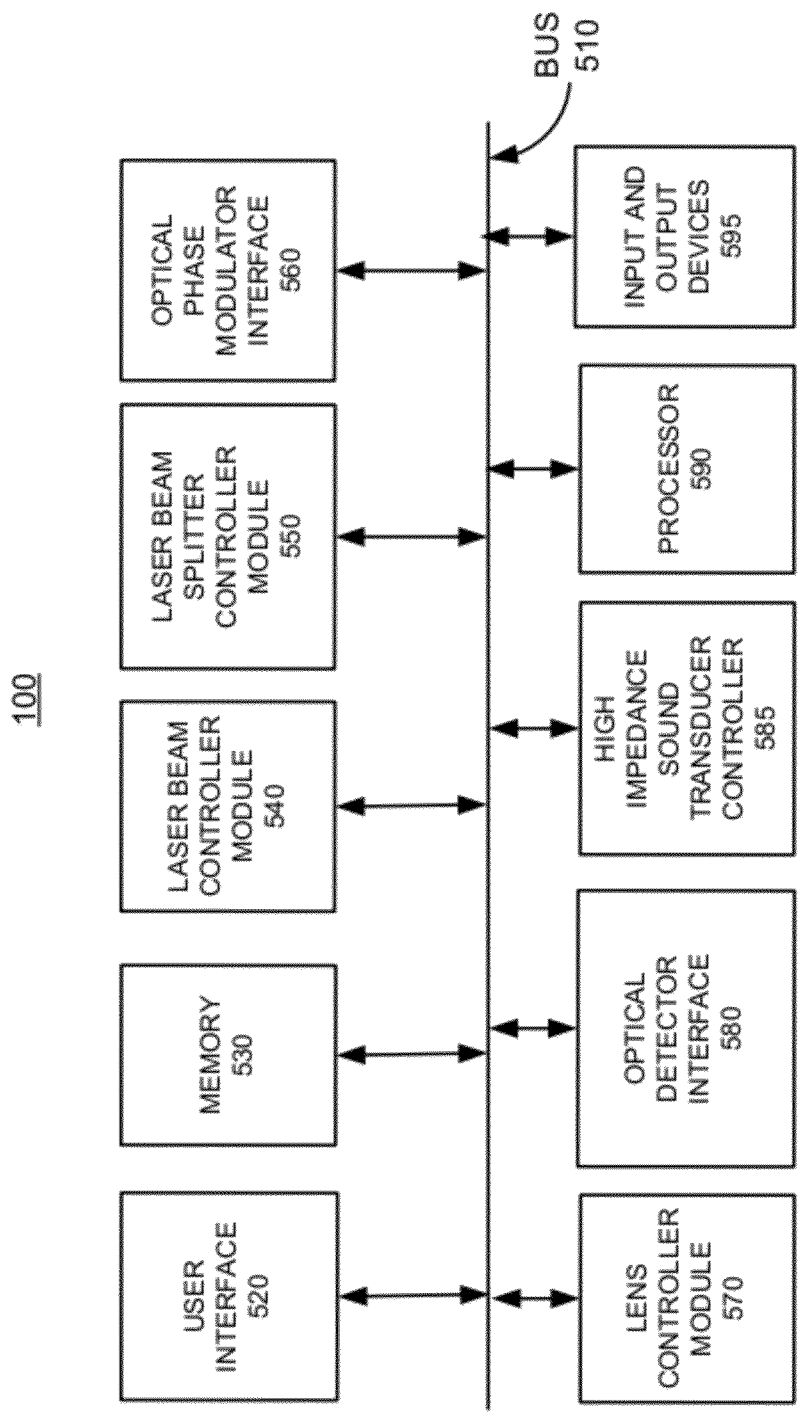
FIG. 5 is a block diagram of a self-diffraction densitometer incorporating an optical homodyne in accordance with a possible embodiment of the disclosure.

FIG. 5 is block diagram of a self-diffraction densitometer incorporating an optical homodyne 100 that may be controlled and operable in a computing environment in accordance with a possible embodiment. The self-diffraction densitometer 100 may include bus 510, user interface 520, memory 530, laser beam controller module 540, laser beam splitter controller module 550, optical phase modulator interface 560, lens controller module 570, optical detector interface 580, high impedance sound transducer controller module 585, processor 590 and input and output devices 595.

Processor 520 may include at least one conventional processor or microprocessor that interprets and executes instructions. Memory 530 may be a random access memory (RAM) or another type of dynamic storage device that stores information and instructions for execution by processor 520. Memory 530 may also include a read-only memory (ROM) which may include a conventional ROM device or another type of static storage device that stores static information and instructions for processor 520.

User interface 520 may enable interaction with and the ability to obtain information from self-diffraction densitometer 100. For example, information about analyte 170 in convergence zone 165 obtained via optical detector interface 580.

ROM may be included in memory 530 to include a conventional ROM device or another type of static storage device that stores static information and instructions for processor 520. A storage device may augment the ROM and may include any type of storage media, such as, for example, magnetic or optical recording media and its corresponding drive.

Input devices 595 may include one or more conventional mechanisms that permit a user to input information to self-diffraction densitometer incorporating an optical homodyne 100, such as a keyboard, a mouse, a pen, a voice recognition device, touchpad, buttons, etc. Output devices 595 may include one or more conventional mechanisms that output information to the user, including a display, a printer, a copier, a scanner, a multi-function device, one or more speakers, or a medium, such as a memory, or a magnetic or optical disk and a corresponding disk drive.

The self-diffraction densitometer incorporating an optical homodyne 100 may perform such functions in response to processor 520 by executing sequences of instructions contained in a computer-readable medium, such as, for example, memory 530. Such instructions may be read into memory 530 from another computer-readable medium, such as a storage device or from a separate device via a communication interface.

Embodiments of the present disclosure may be used for trace chemical detection; such as chemicals associated with explosives and improvised explosive device (IED) detection. It may also be used for screening passengers and be less personally offensive than backscatter x-ray, millimeter wave scanning or a pat down. It may be used to sample air within packages, shipping containers and the like. As it is known that traces of many metabolites are exhaled on a person's breath and relative concentrations are associated with specific medical problems, embodiments of the present invention may further enable improved medical diagnostic detection of traces of specific metabolites on a person's breath. It may also be adapted for use in environmental monitoring.

Although the above description may contain specific details, they should not be construed as limiting the claims in any way. Other configurations of the described embodiments of the disclosure are part of the scope of this disclosure. For example, the principles of the disclosure may be applied to each individual user where each user may individually deploy such a system. This enables each user to utilize the benefits of the disclosure even if any one of the large number of possible applications do not need the functionality described herein. In other words, there may be multiple instances of the components each processing the content in various possible ways. It does not necessarily need to be one system used by all end users. Accordingly, the appended claims and their legal equivalents should only define the disclosure, rather than any specific examples given.

I claim:

1. A method of incorporating an optical homodyne into a self-diffraction densitometer, comprising:
    splitting a laser beam into four beams by passing the laser beam through a plurality of beam splitters;
    passing three beams of the four beams through a lens that focuses the three beams to minimum diffraction limited waist diameter and brings them to convergence at a convergence zone containing an analyte;
    generating a reference beam by passing a fourth beam of the four beams through an optical phase modulator;
    wherein if a medium within the convergence zone absorbs energy at a wavelength of the laser beam, a thermal representation of an interference pattern forms and spatial modulation of temperature results in a spatial modulation of refractive index, whereby a diffracted beam from energy of the three beams is produced into a propagation path of the reference beam; and
    passing the reference beam through the lens and the convergence zone such that the reference beam is coincident with the diffracted beam,
    wherein the reference beam and diffracted beams cyclically go in and out of relative phase and impinge on an optical detector.

2. The method of claim 1, wherein the optical phase modulator is a resonant gas phase acousto-optic modulator.

3. The method of claim 1, further comprising:
    attenuating the reference beam so that it does not drive the optical detector out of its proper operating range.

4. The method of claim 1, wherein the diffracted beam is a signal beam which indicates the extent to which a medium absorbs energy at the wavelength of the laser.

5. The method of claim 4, wherein the optical detector produces an output current that is proportional to a rate at which photons are intercepted and nonlinear mixing of the reference beam coincident with the diffracted beam produce low frequency components in an output current that enable homodyne detection.

6. The method of claim 5, further comprising:
    removing D.C. components from the output current.

7. The method of claim 6, wherein the output current contains A.C. components proportional in amplitude to a product of the reference beam and signal beam amplitudes and wherein a high reference beam amplitude yields high amplitude of A.C. photocurrent components but does not affect thermal noise out of the optical detector.

8. The method of claim 7, further comprising:
    raising the reference beam power to a point where shot noise on the reference beam overpowers the optical detector's thermal noise with a corresponding increase in signal power to enable improvement in signal to noise ratio.

9. The method of claim 1, wherein the convergence zone contains a three dimensional interference pattern.

10. The method of claim 1, wherein the spatial modulation of temperature resulting in the spatial modulation of refractive index constitutes a three dimensional diffraction grating.

11. An apparatus incorporating an optical homodyne into a self-diffraction densitometer, comprising:
    a plurality of beam splitters for splitting a laser beam into four beams;
    a lens through which passes three beams of the four beams to focus the three beams to minimum diffraction limited waist diameter and bring them to convergence at a convergence zone containing an analyte;
    an optical phase modulator through which a fourth beam of the four beams passes to generate a reference beam;
    wherein if a medium within the convergence zone absorbs energy at a wavelength of the laser beam, a thermal representation of an interference pattern forms and spatial modulation of temperature results in a spatial modulation of refractive index, whereby a diffracted beam from energy of the three beams is produced into the propagation path of the reference beam;
    wherein the reference beam passes through the lens and the convergence zone such that the reference beam is coincident with the diffracted beam and the reference beam and diffracted beams cyclically go in and out of relative phase; and
    an optical detector on which the reference beam and the diffracted beam impinge.

12. The apparatus of claim 11, further comprising:
    a second lens to concentrate and direct the reference and diffracted beams through a pin hole prior to impinging the optical detector.

13. The apparatus of claim 11, wherein the optical phase modulator is a resonant gas phase acousto-optic modulator.

14. The apparatus of claim 11, wherein the reference beam is attenuated so that it does not drive the optical detector out of its proper operating range.

15. The apparatus of claim 11, wherein the diffracted beam is a signal beam which indicates the extent to which the medium absorbs energy at the wavelength of the laser and the reference beam coincident with the signal beam has the same wave front curvature and essentially a same divergence.

16. The apparatus of claim 14, wherein the optical detector produces an output current that is proportional to a rate at which photons are intercepted and nonlinear mixing of the reference beam coincident with the diffracted beam produce low frequency components in an output current that enable homodyne detection.

17. The apparatus of claim 15, wherein the D.C. components from the output current are removed and the output current contains A.C. components proportional in amplitude to a product of the reference beam and signal beam amplitudes and wherein a high reference beam amplitude yields high amplitude of A.C. photocurrent components but does not affect thermal noise out of the optical detector.

18. The apparatus of claim 17, wherein the reference beam power is raised to a point where shot noise on the reference beam overpowers the optical detector's thermal noise with a corresponding increase in signal power to enable improvement in signal to noise ratio.

19. A non-transient computer-readable medium storing instructions for incorporating an optical homodyne into a self-diffraction densitometer, the instructions comprising:
    splitting a laser beam into four beams by passing the laser beam through a plurality of beam splitters;

passing three beams of the four beams through a lens that focuses the three beams to minimum diffraction limited waist diameter and brings them to convergence at a convergence zone containing an analyte;

generating a reference beam by passing a fourth beam of the four beams through an optical phase modulator;

wherein if a medium within the convergence zone absorbs energy at a wavelength of the laser beam, a thermal representation of an interference pattern forms and spatial modulation of temperature results in a spatial modulation of refractive index, whereby a diffracted beam from energy of the three beams is produced into a propagation path of the reference beam; and passing the reference beam through the lens and the convergence zone such that the reference beam is coincident with the diffracted beam, wherein the reference beam and diffracted beams cyclically go in and out of relative phase and impinge on an optical detector.

20. The non-transient computer-readable medium of claim 19, wherein the optical phase modulator is a resonant gas phase acousto-optic modulator.

21. The non-transient computer-readable medium of claim 19, further comprising:

attenuating the reference beam so that it does not drive the optical detector out of its proper operating range.

22. The non-transient computer-readable medium of claim 19, wherein the diffracted beam is a signal beam which indicates the extent to which the medium absorbs energy at the wavelength of the laser.

23. The non-transient computer-readable medium of claim 22, wherein the optical detector produces an output current that is proportional to a rate at which photons are intercepted and nonlinear mixing of the reference beam coincident with the diffracted beam produce low frequency components in the output current that enable homodyne detection.

24. The non-transient computer-readable medium of claim 23, further comprising:

removing D.C. components from the output current.

25. The non-transient computer-readable medium of claim 24, wherein the output current contains A.C. components proportional in amplitude to a product of the reference beam and signal beam amplitudes and wherein a high reference beam amplitude yields high amplitude of A.C. photocurrent components but does not affect thermal noise out of the optical detector.

26. The non-transient computer-readable medium of claim 25, further comprising:

raising the reference beam power to a point where shot noise on the reference beam overpowers the optical detector's thermal noise with a corresponding increase in signal power to enable improvement in signal to noise ratio.

* * * * *